US012708523B2

(12) United States Patent
Blanchard

(10) Patent No.: US 12,708,523 B2
(45) Date of Patent: Aug. 18, 2026

(54) 3D PRINTING OF IMPLANTABLE VERTEBRAL SEGMENT

(71) Applicant: Craig Blanchard, Whitney, TX (US)

(72) Inventor: Craig Blanchard, Whitney, TX (US)

(73) Assignee: ESTATE OF CRAIG ALAN BLANCHARD, Richardson, TX (US)

( * ) Notice: Subject to any disclaimer, the term of this patent is extended or adjusted under 35 U.S.C. 154(b) by 0 days.

(21) Appl. No.: 18/757,000

(22) Filed: Jun. 27, 2024

(65) Prior Publication Data

US 2025/0000671 A1 Jan. 2, 2025

Related U.S. Application Data

(60) Provisional application No. 63/510,888, filed on Jun. 28, 2023.

(51) Int. Cl.
*A61F 2/44* (2006.01)
*A61F 2/46* (2006.01)

(52) U.S. Cl.
CPC .............. *A61F 2/4465* (2013.01); *A61F 2/44* (2013.01); *A61F 2002/443* (2013.01); *A61F 2/4611* (2013.01); *A61F 2310/00023* (2013.01)

(58) Field of Classification Search
CPC .............. A61F 2/44; A61F 2002/30985; A61F 2/4455–2/447
See application file for complete search history.

(56) References Cited

U.S. PATENT DOCUMENTS 6,039,763 A * 3/2000 Shelokov .............. A61F 2/4425 623/17.16
2014/0163682 A1* 6/2014 Iott ....................... A61F 2/4455 623/17.15
2019/0029842 A1* 1/2019 Xiao ....................... A61L 27/56
2019/0183654 A1* 6/2019 Arramon ............... A61F 2/4425
2020/0188134 A1* 6/2020 Mullen ..................... A61F 2/34
2022/0354660 A1* 11/2022 De Pablos Almazan .................... A61F 2/44

FOREIGN PATENT DOCUMENTS

CN 105534622 A * 5/2016 ............... A61F 2/44
CN 113940796 A * 1/2022 ............... A61F 2/44

OTHER PUBLICATIONS

English-language translation of CN 105534622 A (2016); accessed Aug. 4, 2025.*
English-language translation of CN 113940796 A (2022); accessed Aug. 4, 2025.*

* cited by examiner

*Primary Examiner* — Julianna N Harvey
(74) *Attorney, Agent, or Firm* — Barry Choobin; Patent 360

(57) ABSTRACT

An implantable vertebral segment for replacing a damaged vertebral segment in a patient. The implantable vertebral segment includes a vertebral bone member and a vertebral disc member. The vertebral bone member includes an outer portion and an inner portion. The outer portion is configured to be coupled to the inner portion through a fastening mechanism, wherein the outer portion and the inner portion form a tunnel configured to receive a spinal cord. Also, the vertebral bone member and the vertebral disc member include an interlocking mechanism for coupling the vertebral bone member and the vertebral disc member.

9 Claims, 4 Drawing Sheets

3D PRINTING OF IMPLANTABLE VERTEBRAL SEGMENT

CROSS-REFERENCE TO RELATED APPLICATIONS

This application claims priority from a U.S. Provisional Patent Appl. No. 63/510,888, filed on Jun. 28, 2023, which is incorporated herein by reference in its entirety.

FIELD OF INVENTION

The present invention relates to implantable vertebral segments, and more particularly, the present invention relates to a 3D printing of implantable vertebral segments, for replacement.

BACKGROUND

Vertebral bone defects can occur due to a variety of reasons, such as degenerative spine conditions, spinal deformity, accidents, and spinal infections. Such defects are corrected through spinal surgery. Often a need arises for implantation or bone grafting. Typically, a portion of vertebral bone is implanted which grows and fuses over time. Also, many types of artificial bone implants are known for use in different conditions. However, bone implants are not always fully compatible, for example, shape and size may not be correct. Also, the fusion of bones results in rigidity, and the flexibility of the spine is compromised. This often results in poor results and may require multiple surgeries. Multiple surgeries increase the risk of spinal injury as well as exponentially increase the overall costs.

A need is therefore appreciated for a method for manufacturing perfectly sized vertebral bones and discs for implantation.

SUMMARY OF THE INVENTION

The following presents a simplified summary of one or more embodiments of the present invention to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a 3D printed implantable vertebral segment that can replace the damaged vertebral segment in a patient.

Another object of the present invention is that the 3D printed vertebral parts correspond to the vertebrae of the patient in terms of size and shape of undamaged vertebrae of the patient.

Still, another object of the present invention is that the 3D-printed vertebral parts are biocompatible and safe.

A further object of the present invention is that the flexibility of the vertebral could be restored.

Still, a further object of the present invention is that the surgical process of implantation can be made easier.

Yet a further object of the present invention is that the recovery period after surgery can be made shorter.

An additional object of the present invention is that severe vertebral damage can be treated by replacement.

In one aspect, disclosed is an implantable vertebral segment comprising a vertebral disc member. The vertebral bone member comprises an outer unit, and an inner unit, wherein the outer unit is configured to be coupled to the inner unit through a fastening mechanism, wherein the outer unit and the inner unit form a tunnel configured to receive a spinal cord. The vertebral bone member is 3D printed. The vertebral bone member is made of titanium. The vertebral disc member is 3D printed. The vertebral disc member is made of rubber. The vertebral bone member and the vertebral disc member comprise an interlocking mechanism for coupling the vertebral bone member and the vertebral disc member.

In one aspect, disclosed is a method for correcting backbone defects in a patient, the method comprising imaging a backbone of the patient to generate a model specific to the patient; and 3D printing an implantable vertebral segment based on the model.

BRIEF DESCRIPTION OF DRAWINGS

The accompanying figures, which are incorporated herein, form part of the specification and illustrate embodiments of the present invention. Together with the description, the figures further explain the principles of the present invention and enable a person skilled in the relevant arts to make and use the invention.

DETAILED DESCRIPTION

Figure 1:
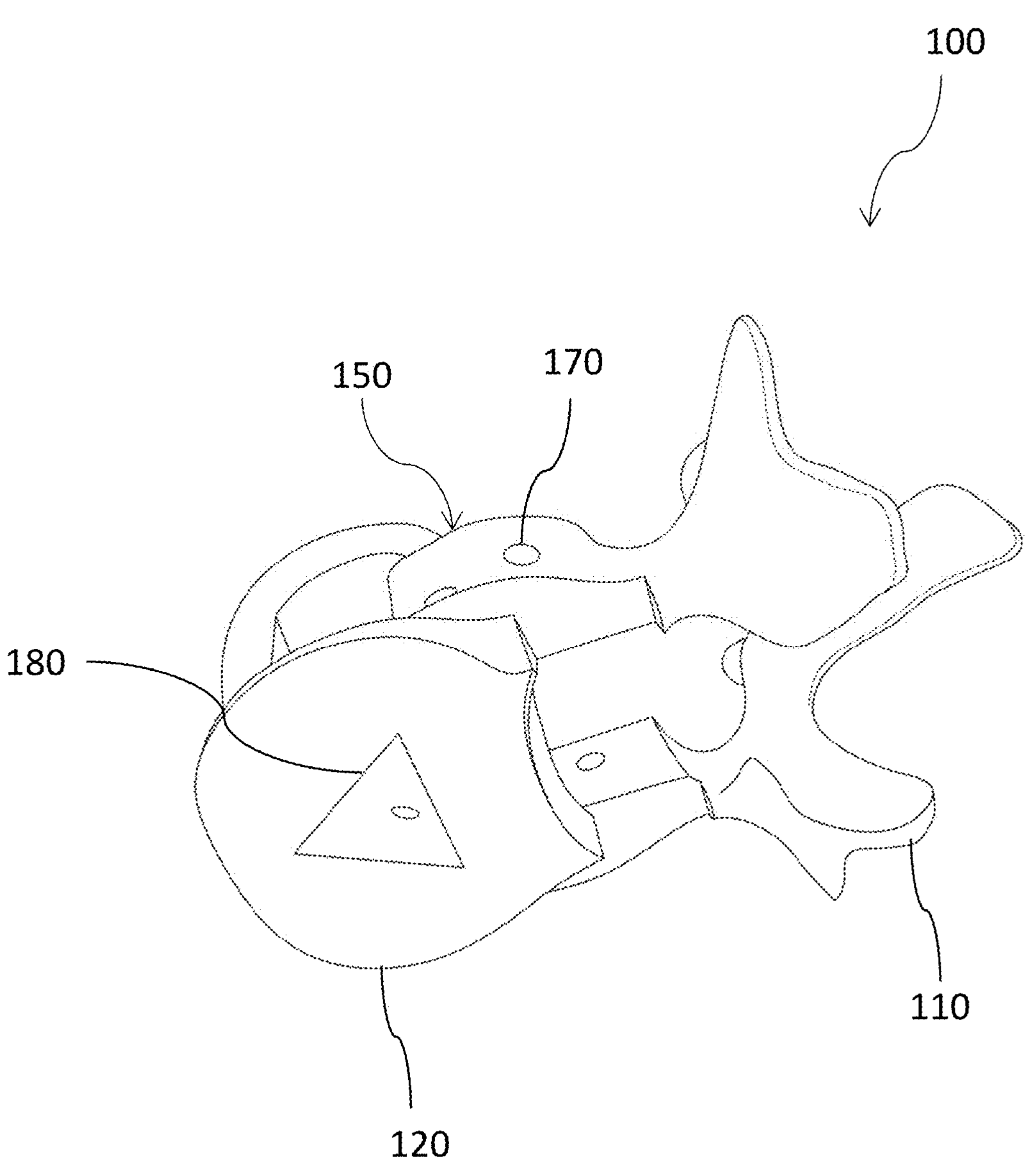
FIG. 1 shows a vertebral bone member in a partially open state, according to an exemplary embodiment of the present invention.

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word “exemplary” is used herein to mean “serving as an example, instance, or illustration.” Any embodiment described herein as “exemplary” is not necessarily to be construed as preferred or advantageous over other embodiments. Likewise, the term “embodiments of the present invention" does not require that all embodiments of the invention include the discussed feature, advantage or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprise", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely to illustrate the general principles of the invention since the scope of the invention will be best defined by the allowed claims of any resulting patent.

The described invention pertains to a 3D printing of implantable vertebral segments. Also, the described invention pertains to the 3D printing of vertebral bone members and disc members. Also, disclosed is a method for implanting the 3D printed implantable vertebral segments. The vertebral bone members and disc members are also referred to herein as vertebral parts. Also, the described invention pertains to the vertebral parts made by the 3D printing process. The disclosed method allows the manufacturing of vertebral parts as per the specifications of a patient's back as it existed before any injury. The implant according to the present invention is compatible and prevents the need for multiple surgeries. The specification for a patient can be determined through various imaging techniques, such as MRI. The backbone of a patient can be modeled using non-invasive imaging techniques to prepare a 3D model specific to a patient. Using the model, the vertebral parts can be 3D printed.

The advantage of the present invention is that the 3D-printed vertebral segments implanted in the backbone of a patient may duplicate that which existed before the spinal injury or damaged portion of the backbone. This makes the process of spinal surgery easier and quicker, and significantly increases the chances of successful surgery. The 3D printed vertebral parts allow replacing the damaged vertebral bone and discs of the backbone of a patient, rather than manipulating existing bone structures. Thus, the claimed process and 3D-printed vertebral parts provide a new and more efficient way of treating spinal disorders using spinal surgery. Through spinal surgery, the existing and damaged vertebral structures can be replaced by a 3D-printed vertebral segment with materials that are biocompatible to the patient's body. Using the disclosed method, severe backbone damage can be corrected. The imaging techniques, like MRI, allow modeling a perfect match for a patient.

In certain implementations, the vertebral bone members can be made from titanium and the vertebral disc members can be made from a biocompatible hard rubber-like substance. It is to be understood that any other biocompatible and suitable material is within the scope of the present invention. Also, other materials required for 3D printing can be used without departing from the scope of the present invention.

Using the disclosed 3D printing of vertebral parts, the damaged spine portions can be replaced. Unlike the conventional bone fusion techniques which are complex, and often restrict the activities and movements of the patient that were previously capable, replacing the bone or disc can eliminate such complex steps. Also, the functionality of the backbone can be significantly restored including the flexibility and cushioning.

In certain implementations, disclosed is an implantable vertebral segment and a method of preparing the implantable vertebral segments using 3D printing. In one implementation, the implantable vertebral segment includes vertebral bone and disc members extending between L1 and L5 of a human vertebra.

In certain implementations, disclosed is a method for replacing lumbar portion (L1 to L5) using 3D printed implantable vertebral segment. Replacing the lumbar portion ensures the flexibility of the backbone compared to the conventional bone fusion techniques. Also, the fusion process requires complex surgery and long recovery times. The disclosed method allows replacing the whole lumbar portion, preventing any complexities, and the recovery can be quicker.

In certain implementations, the disclosed method uses a variety of diagnostic and imaging techniques to model the backbone. The model can be used for 3D printing the vertebral parts for implantation.

In certain implementations, disclosed are an assembly and method for replacing a vertebral segment in a patient with a 3D printed implantable vertebral segment. The disclosed invention can provide a functional spine with flexibility and cushioning. The disclosed assembly includes a locking system that can keep the implanted vertebral segment from shifting in any direction.

Figures 2A, 2B:
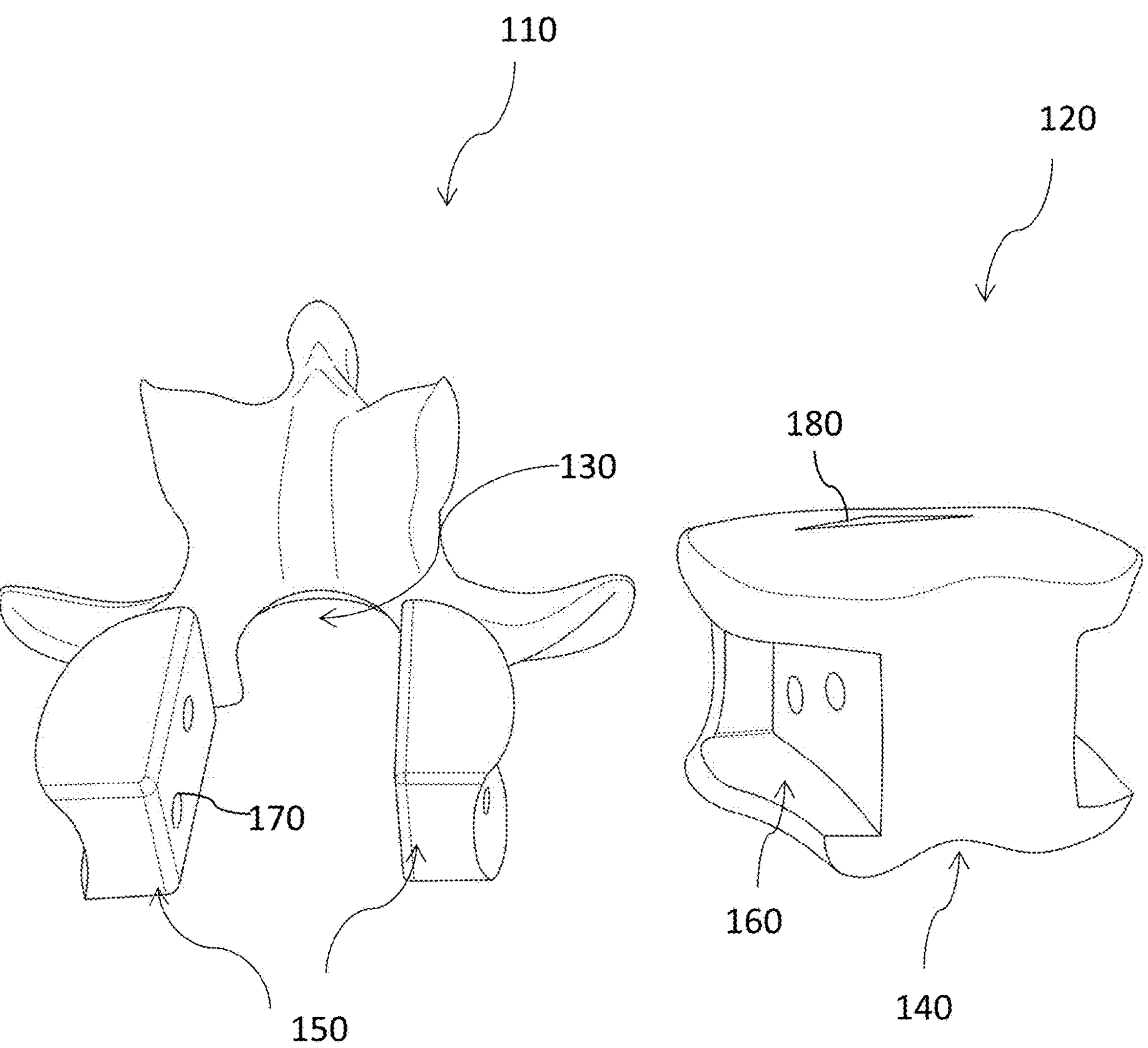
FIG. 2A shows an outer unit of the vertebral bone member, according to an exemplary embodiment of the present invention.
FIG. 2B shows an inner unit of the vertebral bone member, according to an exemplary embodiment of the present invention.
Figure 3A:
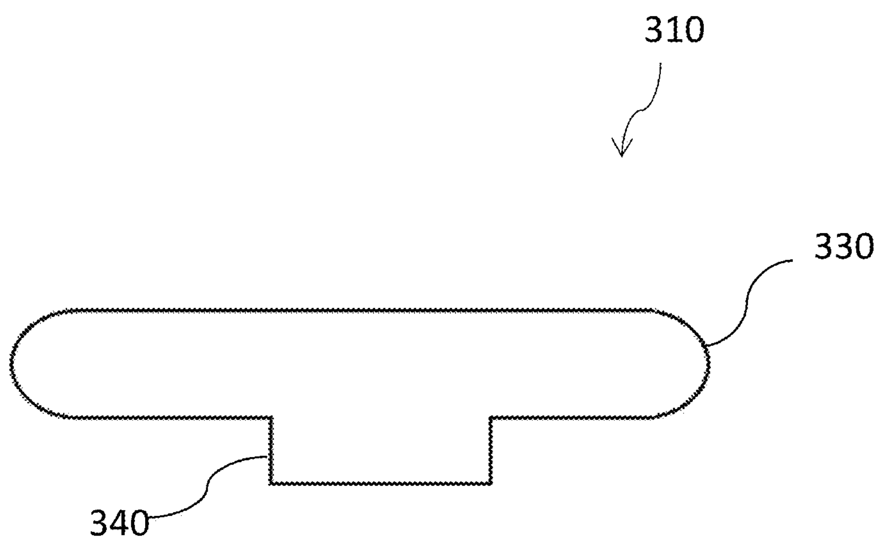
FIG. 3A shows a vertebral disc member, according to an exemplary embodiment of the present invention.
Figure 3B:
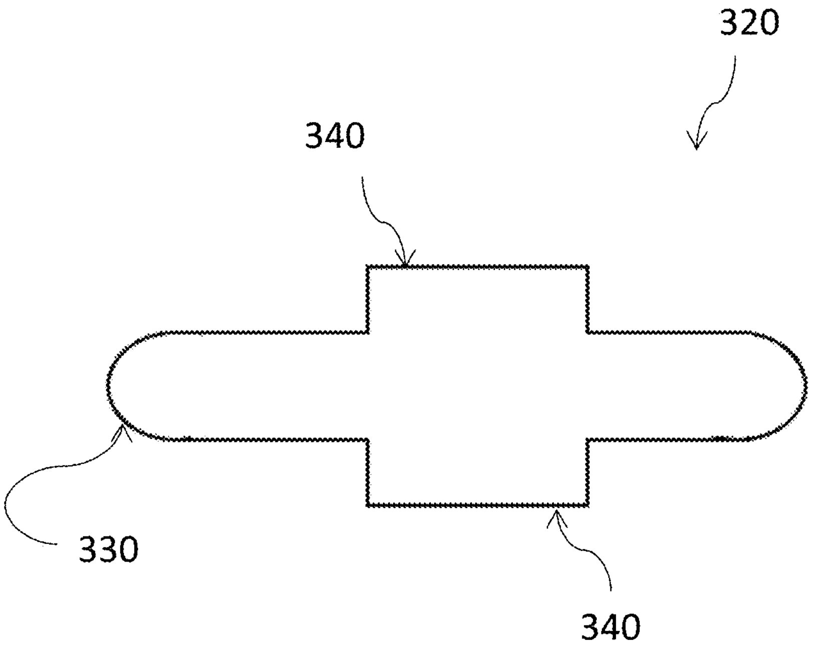
FIG. 3B shows a vertebral disc member, according to an exemplary embodiment of the present invention.

Referring to FIG. 1 shows an exemplary embodiment of the vertebral bone member 100 including an outer unit 110 and an inner unit 120. FIG. 2A shows the outer unit 110 and FIG. 2B shows the inner unit 120. The assembly includes a vertebral bone member 100 that includes an outer unit 110 and an inner portion 120. The assembly further includes a 3D-printed vertebral disc member that can replace the intervertebral disc. FIGS. 3A and 3B shows an implementation of vertebral disc member, wherein FIG. 3A shows the vertebral disc member 310 for capping ends of the implantable vertebral segment and FIG. 3B shows the vertebral disc member 320 that can be sandwiched between two vertebral bone members. The 3D-printed vertebral disc member can be sandwiched between two vertebral bone members as a vertebral disc. Each of the vertebral disc members can include a central disc portion 330 and a triangular protrusion 340 protruding vertically from a central top area of the central disc portion. The vertebral disc member 310 has only one protrusion 340 while the opposite surface is plane. The vertebral disc member 320 has the protrusion 340 on both its upper side and the bottom side. The inner unit of the vertebral bone member can include a triangular groove that can receive protrusion 340 for interlocking the vertebral disc member and the vertebral bone member together creating the vertebral segment. The vertebral bone member can be coupled to the vertebral disc member through the interlocking of the triangular protrusion 340 and the triangular groove 180. The triangular interlocking can prevent the movement of the vertebral bone member relative to the vertebral disc member but allows for flexibility like a normal backbone.

Figure 4:
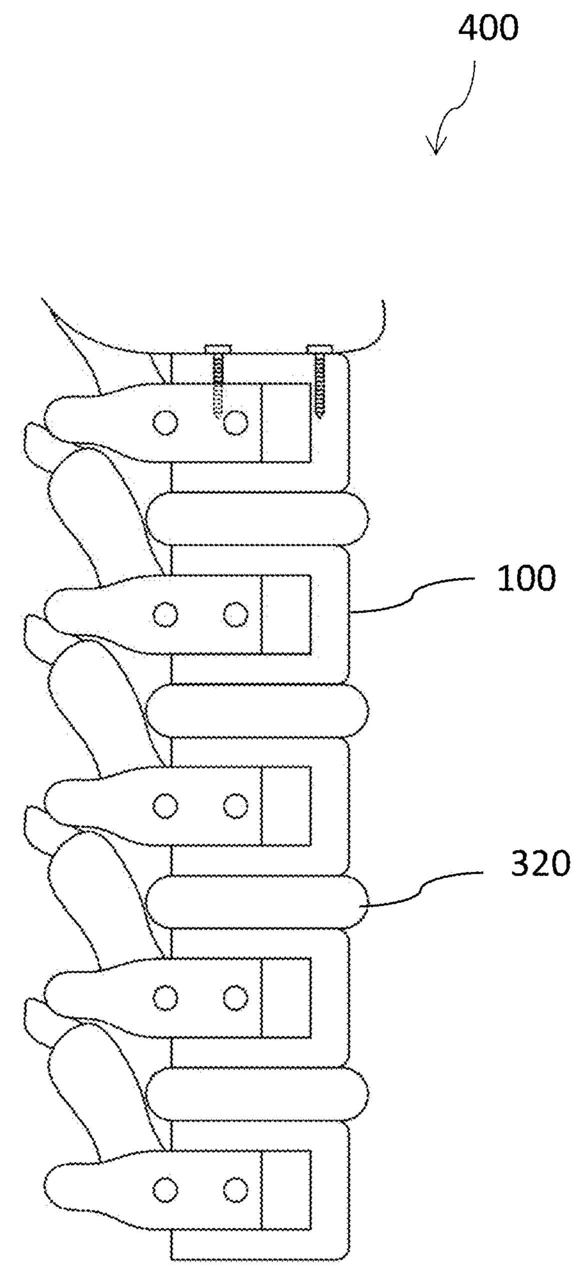
FIG. 4 shows an implantable vertebral segment made from vertebral bone and disc members, according to an exemplary embodiment of the present invention.

Again, referring to FIGS. 2A and 2B, the outer unit 110 of the vertebral bone member 100 may include a cutout 130 on its rear side for receiving at least a portion of the spinal cord. Similarly, the inner unit 120 of the vertebral bone member 100 may include a cutout 140 that corresponds with the cutout 130 in the outer unit such that the two cutouts 130 and 140 in the outer unit and the inner unit can form a tunnel that can receive the spinal cord. The implantable vertebral segment 400, shown in FIG. 4, can protect the spinal cord without putting any pressure on the spinal cord. Also, the triangular interlocking between the vertebral bone member and the vertebral disc member may prevent any pressure or force on the spinal cord during implantation surgery and post-surgery. The implantable vertebral segment can wrap around the spinal cord protecting the same and providing structural support.

In certain implementations, the outer unit 110 and the inner unit 120 of the vertebral bone member 100 can be coupled to each other through a suitable fastening mechanism. The fastening mechanism may include a socket 160 and plug 150 that can interlock with each other to secure the two units of the vertebral bone member 100. For example, the inner unit can include a socket 160 while the outer unit may include the plug 150. The plug 150 may snugly fit into the socket 160. The fastening mechanism including the plug and socket, can further be secured using a snap-fit-like mechanism. It is to be understood that any other fastening mechanism is within the scope of the present invention. Also, the two interlocked units 110 and 120 of the vertebral bone member 100 can be further secured using screws, for example, counter-sunk screws. FIGS. 2A and 2B shows the holes 170 for the screws. The screws can also be used to secure the implanted vertebral segment 400 to the vertebra of the patient.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A method for correcting spinal defects in a patient, the method comprising:

imaging a spine of the patient to generate a model specific to the patient; and 3D printing an implantable vertebral segment based on the model, wherein the implantable vertebral segment comprises:

a vertebral bone member comprising:

an outer unit, and an inner unit, wherein the outer unit is configured to be coupled to the inner unit through a fastening mechanism, the outer unit and the inner unit together forming a tunnel configured to receive a spinal cord, and the fastening mechanism comprising a plug and socket that interlock to secure the outer unit with the inner unit;

a vertebral disc member, wherein the vertebral disc member comprises a central disc portion, an upper triangular protrusion extending vertically from a central top area of the central disc portion, and a lower triangular protrusion extending vertically from a central bottom area of the central disc portion;

wherein the vertebral bone member comprises a first vertebral bone member and a second vertebral bone member, wherein the vertebral disc member is physically positioned between and mechanically interlocked with the first vertebral bone member and the second vertebral bone member; and implanting the implantable vertebral segment at a location of a damaged vertebral bone and an adjacent vertebral disc, wherein the implantable vertebral segment is biocompatible and anatomically similar to the vertebral bone and disc before damage.

2. The method of claim 1, wherein the vertebral bone member is made of titanium.

3. The method of claim 2, wherein the vertebral disc member is made of a biocompatible hard rubber substance.

4. The method of claim 1, wherein the vertebral bone member and the vertebral disc member comprise complementary interlocking features configured to mechanically couple the vertebral bone member and the vertebral disc member.

5. The method of claim 1, wherein a lumbar vertebral portion of the patient is replaced with the implantable vertebral segment.

6. The method of claim 1, wherein the implantable vertebral segment further comprises a capping vertebral disc member configured to cap an outer end of one of the first vertebral bone member or the second vertebral bone member.

7. The method of claim 1, wherein each of the upper triangular protrusion and the lower triangular protrusion is configured to fit into a respective triangular groove formed in the inner units of the first vertebral bone member and the second vertebral bone member.

8. A method for correcting spinal defects in a patient, the method comprising:

imaging a spine of the patient to generate a model specific to the patient; and 3D printing an implantable vertebral segment based on the model, wherein the implantable vertebral segment comprises:

a vertebral bone member comprising:

an outer unit, and an inner unit, wherein the outer unit is configured to be coupled to the inner unit through a fastening mechanism, the outer unit and the inner unit together forming a tunnel configured to receive a spinal cord, and the fastening mechanism comprising a plug and socket that interlock to secure the outer unit with the inner unit;

a vertebral disc member;

wherein the vertebral bone member comprises a first vertebral bone member and a second vertebral bone member and a second vertebral bone member, wherein the vertebral disc member is physically positioned between and mechanically interlocked with the first vertebral bone member and the second vertebral bone member; and a capping vertebral disc member configured to cap an outer end of one of the first vertebral bone member or the second vertebral bone member, the capping vertebral disc member comprising a central disc portion and an upper triangular protrusion extending vertically from a central top area of the central disc portion; and implanting the implantable vertebral segment at a location of a damaged vertebral bone and an adjacent vertebral disc, wherein the implantable vertebral segment is biocompatible and anatomically similar to the vertebral bone and disc before damage.

9. The method of claim 8, wherein the upper triangular protrusion is configured to fit into a triangular groove formed in the inner unit of the first vertebral bone member or the second vertebral bone member.

* * * * *